United States Patent
Gaponyuk et al.

(12) 
(10) Patent No.: US 6,635,243 B1
(45) Date of Patent: Oct. 21, 2003

(54) ANTIVIRAL NASAL DROPS COMPRISING RECOMBINANT INTERFERON A BIOCOMPATIBLE POLYMER AND AN ANTIOXIDANT

(76) Inventors: Petr Jakovlevich Gaponyuk, Caulfield North, AU-3161 Melbourne, VIC (AU); Elena Alexeevna Markova, Caulfield North, AU-3161 Melbourne, VIC (AU); Iliya Alexandrovich Markov, 121614, 7-1-32 Krylatskie Holmy, Moscow (RU)

( * ) Notice: Subject to any disclaimer, the term of this patent is extended or adjusted under 35 U.S.C. 154(b) by 0 days.

(21) Appl. No.: 09/936,470

(22) PCT Filed: Sep. 6, 1999

(86) PCT No.: PCT/RU99/00320

§ 371 (c)(1),
(2), (4) Date: Dec. 18, 2001

(87) PCT Pub. No.: WO00/54798

PCT Pub. Date: Sep. 21, 2000

(30) Foreign Application Priority Data

Mar. 16, 1999 (RU) .......................................... 99100666

(51) Int. Cl.$^7$ ........................ A61K 38/21; A61K 31/74; A61K 31/79

(52) U.S. Cl. .................... 424/85.4; 424/85.5; 424/85.6; 424/85.7; 424/78.07

(58) Field of Search .............................. 424/85.4, 85.5, 424/85.6, 85.7, 78.07

(56) References Cited

U.S. PATENT DOCUMENTS

| | | | | |
|---|---|---|---|---|
| 4,647,454 A | * | 3/1987 | Cymbalista | 424/80 |
| 4,710,376 A | * | 12/1987 | Evans et al. | 424/83 |
| 4,855,238 A | * | 8/1989 | Gray et al. | 435/243 |

FOREIGN PATENT DOCUMENTS

| | | |
|---|---|---|
| RU | 2020957 | 10/1994 |
| RU | 2022562 | 11/1994 |
| RU | 2033180 | 4/1995 |
| RU | 2057544 | 4/1996 |
| RU | 2073522 | 2/1997 |
| RU | 2077336 | 4/1997 |
| RU | 2095081 | 11/1997 |
| RU | 2097061 | 11/1997 |
| RU | 2108804 | 4/1998 |
| WO | 9321229 | 10/1993 |

OTHER PUBLICATIONS

Ershov F.I., *Medicina*, p. 216 (1996).

* cited by examiner

*Primary Examiner*—Elizabeth Kemmerer
*Assistant Examiner*—Ruixiang Li
(74) *Attorney, Agent, or Firm*—Ladas & Parry

(57) ABSTRACT

The present invention can be used in pharmacology specifically in the preparation of interferon-containing compositions, which are capable of conserving their biological activity and can be administrated intranasally, e.g. in the preparation of nasal drops. This invention essentially refers to an antiviral agent in the form of nasal drops that contains a genetically engineered alpha, beta or gamma interferon with a viscosity of (1.1–30.0)* 10 Pascal ·second, a biocompatible polymer and a buffer mixture. The agent may further include an antioxidant, and the ingredients are contained in the following amounts per ml buffer mixture: 1,000 to 5,000 IU of genetically engineered interferon; 0.005 to 0.714 g of biocompatible polymer; and 0.0001 to 0.0008 g of an antioxidant. TRILON B® (disodium salt of EDTA) is used as the antioxidant, whereas polyvinylpyrrolidone and/or polyethylene oxide is (are) used as the biocompatible polymer(s) at polyvinylpyrrolidone/ polyethylene oxide ratio of 1:1–50.

7 Claims, No Drawings

ANTIVIRAL NASAL DROPS COMPRISING RECOMBINANT INTERFERON A BIOCOMPATIBLE POLYMER AND AN ANTIOXIDANT

CROSS REFERENCES TO RELATED APPLICATIONS

The present application claims the benefit of priority of PCT International Application No. PCT/RU99/00320, filed on Sep. 6, 1999, which claims priority from Russian Federation patent application No. 9910066, filed Mar. 16, 1999.

FIELD OF THE INVENTION

The present invention can be used in pharmacology specifically in the preparation of interferon-containing compositions, which are capable of conserving their biological activity and can be administrated intranasally, e.g. in the preparation of nasal drops.

BACKGROUND OF THE INVENTION

Medicines containing interferons (natural, recombinant or genetically engineered) are widely used. Interferon-containing preparations, in addition to antiviral effects, cause strong immunomodulatory effects that induce several positive homeostatic shifts, antitumour effects, etc. (RU, Application 940942742 Cl. A 61 K 38/21, 1997. RU, patent 20957544, Cl. A 61 K 38/21, 1996).

In Russia, natural human interferons derived from leukocytes have been widely used for the treatment and prevention of influenza and acute viral respiratory infections (AVRI) since the late 1960s. This interferon was manufactured from expensive donor blood leukocyte preparations (RU, Patent 2033180, Cl. A 61 K 38/21, 1995. SU, Inventor's Certificate 297296, Cl. A 61 K 36/21, 1977. RU, patent 2108804, Cl. A 61 K 38/21, 1996).

Medicines prepared from leukocytes or any other component of human blood are potentially hazardous and can transmit viral infection (hepatitis, herpes virus, cytomegalovirus, AIDS, slow infections etc.).

Because of this, recombinant and genetically engineered interferon preparations of the highest purification (up to 98% pure) are increasingly used for clinical purposes (FS 42-3279-96, VFS 42-2989-97, RU, Patent 2073522, Cl. A 61 38/21, 1997. Ershov, F.I., Sistema interferona v norme i pri patologii (The Interferon System under Normal and Pathological Conditions); Moscow: Medicina, 1966, p.216.

These preparations are effective in treating oncological diseases by parenteral administration of high doses (3–10 million IU or more per 24 h) in repeated long courses. However, such doses often cause side effects, such as disorders haemopoiesis, suppression of the immune system, formation of anti-interferon antibodies etc.

However, the recent experience with clinical administration of interferons suggests that their efficacy can be increased by using appropriate drug forms (with account taken of the specific pathogenetic features of the diseases) designed to deliver high concentrations of interferon to the focus of viral infection. After such an administration, interferon causes antiviral and immunomodulatory effects without cytostatic or other side effects. This makes it expedient to develop various drug forms containing interferons designed for topical administration (suppositories, ointments, drops, aerosols, etc.) The closest analogue of this invention, in terms of the nature of the drug and achieved result, is an antiviral drug form for intranasal administration containing human interferon, a biocompatible polymer (6% Polyglucin), and a buffer mixture with the following contents of ingredients per ml solution:

| Interferon | (1–6.6) .10 IU |
| Biocompatible polymer (Polyglucin) | 5–30 |
| Buffer mixture | pH 7.0–7.6 in solution |

(RU. Patent 2095081, Cl. A 61 K 38/21, 1977).

However, intranasal drug forms containing recombinant or genetically engineered interferons have not been developed in Russia.

SUMMARY OF THE INVENTION

The main idea of this invention was to develop of an antiviral drug form (nasal drops) containing a genetically engineered interferon, which would allow a prolonged contact with nasal mucous, act topically at the site of primary invasion and reproduction of influenza and other respiratory viruses, be easily absorbable, and have an optimal viscosity permitting the drug to spread over the mucous and be retained on it for a long time.

To solver this problem, we developed an antiviral drug (nasal drops) containig a liquid interferon preparation (a genetically engineered alpha, beta or gamma interferon with viscosity of $(1.1–30.0)*10$ Pascal second). The antiviral drug contains a biocompatible polymer, antioxidant, and buffer mixture with the following contents of ingredients per ml buffer mixture:

| Genetically engineered interferon | 1000–50,000 IU |
| Biocompatible polymer | 0.005–0.714 g |
| Antioxidant | 0.0001–0.0008 g |

TRILON B® (disodium salt of ethylenediaminetetraacetic acid ("EDTA")) is used as an antioxidant, and polyvinylpyrrolidone and/or polyethylene oxide is used as a biocompatible polymer. The drug described here contains polyvinylpyrrolidone and polyethylene oxide at a ratio of 1:1–50.

DETAILED DESCRIPTION OF THE PREFERRED EMBODIMENTS

Variant 1. The technology of manufactured this drug (nasal drops) is the same for all variants described below. Prepare solutions of the following ingredients in separate containers: 50% polyethylene oxide, 6% polyvinylpyrrolidone and 10% aqueous TRILON B® (disodium salt of EDTA). Filter the solutions. Use phosphate-buffered saline as a solvent. Add these solutions to a manufacturing vessel in the specified sequence, and sterilize. Then add genetically engineered interferon. Mix the ingredients. Dispense the solution into appropriate containers, hermetically seal and label.

Suggested composition of the antiviral drug:
Each milliliter of the buffer mixture contains:

| | |
|---|---|
| Genetically engineered interferon beta | 500,000 IU |
| Polyvinylpyrrolidone | 0.014 g |
| Polyethylene oxide | 0.7 g |
| TRILON B ® (disodium salt of EDTA) | 0.0008 g |
| Viscosity of solution | 30.0*10 Pascal · second |

Variant 2. Proceed as described under Variant 1.
Suggested composition of the antiviral drug:
Each milliliter of the buffer mixture contains:

| | |
|---|---|
| Genetically engineered interferon alpha | 10,000 IU |
| Polyvinylpyrrolidone | 0.01 g |
| Polyethylene oxide | 0.1 g |
| TRILON B ® (disodium salt of EDTA) | 0.0004 g |
| Viscosity of solution | 3.0*10 Pascal · second |

Variant 3. Proceed as described under Variant 1.
Suggested composition of the antiviral drug:
Each milliliter of the buffer mixture contains:

| | |
|---|---|
| Genetically engineered interferon gamma | 1,000 IU |
| Polyvinylpyrrolidone | 0.05 g |
| TRILON B ® (disodium salt of EDTA) | 0.0001 g |
| Viscosity of solution | 1.1*10 Pascal · second |

Feasibility of Industrial-Scale Manufacture

The antiviral drug (nasal drops) obtained as described in the previous section has the appearance of a clear liquid whose viscosity differs between variants. Laboratory tests performed on cultured animal cells showed that the drug is not toxic and fully conserves its antiviral activity.

Clinical tests on 59 volunteers of 18–20 years showed that the drug is safe, well-tolerated, and does not induce the formation of anti-interferon antibodies. It is administrated in nasal drops for treating acute respiratory disease and influence. For prophylaxis of respiratory diseases, the drug is administrated intranasally two times a day (2–3 drops into each nostril) during the whole period of contact with a patient (each drop is equivalent to 500 IU). For the treatment of influenza, the drug is administrated at dose of 2–3 drops into each nostril every 3–4 hours for 5 days.

What is claimed is:

1. An antiviral drug presented as nasal drops comprising genetically engineered alpha, beta or gamma interferon, at least one biocompatible polymer selected from the group consisting of polyvinyl pyrrolidone and polyethylene oxide, and a biocompatible antioxidant the drug viscosity being 11–300 Pascal ·second.

2. The antiviral drug of claim 1 wherein the antioxidant is TRILON B® (disodium salt of ethylenediaminetetraacetic acid).

3. The antiviral drug of claim 1 or claim 2 comprising polyvinyl pyrrolidone and polyethylene oxide in a ratio of 1:1 to 1:50.

4. An antiviral drug presented as nasal drops comprising per ml of a buffered saline solution:

| | | |
|---|---|---|
| a. | genetically engineered alpha, beta or gamma interferon | 1,000–300,000 IU |
| b. | at least one biocompatible polymer selected from the group consisting of polyvinyl pyrrolidone and polyethylene oxide | 0.005–0.714 g |
| c. | antioxidant | 0.0001–0.0008 g |
| | the drug viscosity being 11–300 Pascal · second. | |

5. The antiviral drug of claim 4 wherein the antioxidant is TRILON B® (disodium salt of ethylenediaminetetraacetic acid).

6. The antiviral drug of claim 4 or claim 5 comprising polyvinyl pyrrolidone and polyethylene oxide.

7. The antiviral drug of claim 4 or claim 5 comprising polyvinyl pyrrolidone and polyethylene oxide in a ratio of 1:1 to 1:50.

* * * * *